(12) United States Patent
Cruise

(10) Patent No.: US 6,537,569 B2
(45) Date of Patent: Mar. 25, 2003

(54) RADIATION CROSS-LINKED HYDROGELS

(75) Inventor: Gregory M. Cruise, Rancho Santa Margarita, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 0 days.

(21) Appl. No.: 09/783,762

(22) Filed: Feb. 14, 2001

(65) Prior Publication Data

US 2002/0111392 A1 Aug. 15, 2002

(51) Int. Cl.$^7$ .................................................. A61F 2/02
(52) U.S. Cl. ..................................... 424/426; 514/772.3
(58) Field of Search ................................ 424/423, 426; 514/772.3

(56) References Cited

U.S. PATENT DOCUMENTS

| | | | |
|---|---|---|---|
| 5,354,790 A | | 10/1994 | Keusch et al. |
| 5,634,943 A | * | 6/1997 | Villain et al. .................. 623/5 |
| 5,752,974 A | | 5/1998 | Rhee et al. |
| 6,060,582 A | * | 5/2000 | Hubbell et al. ............. 528/354 |

OTHER PUBLICATIONS

Samdeep Kumar, Bert O. Haglund, and Kenneth J. Himmelstein, In Situ–Forming Gels for Ophthalmic Drug Delivery, 1994, p. 47–55, vol. 10, No. 1, Mary Ann Liebert, INc., Omaha, Nebraska.

Olliver Laccourreye, MD, Alexandre Laurent, MD, Marc Polivka, MD, Michel Wassef, MD, Laurent Domas, Daniel Brasnu, MD, and Jean Jacoues Merland, MD, Biodegradable Starch Microspheres for Cerebral Arterial Embolization, Feb. 1993, p. 150–154, vol. 2.

Ashok J. Kumar, Stephen L. Kaufman, Jerry Patt, John B. Posey, Daniel D. Maxwell, and Robert I. White, Jr., Preoperative Embolization of Hypervascular Head and Neck Neoplasms Using Microfibrillar Collagen, Mar./Apr. 1982, p. 163–168, vol. 3, AJNR.

Fabrizio Duranti, MD, Giovannie Salti, MD, Bruno Bovani, MD, PHD, Mario Calandra, MD, Maria Laura Rosati, MD,PHD, Injectable Hyaluronic Acid Gel for Soft Tissue Augmentation A Clinical and Histological Study, 1998, p. 1317–1325, vol. 24, Elsevier Science Inc.

* cited by examiner

*Primary Examiner*—Carlos Azpuru
(74) *Attorney, Agent, or Firm*—Robert D. Buyan; Stout, Uxa, Buyan & Mullins, LLP

(57) ABSTRACT

Radiation-crosslinked, biodrgradable, synthetic hydrogels and their use in various applications, including certain medical applications wherein the hydrogel(s) are implanted on or in the body of a human or animal patient. Radiation-crosslinked, biodrgradable, synthetic hydrogels of this invention may be prepared by irradiating monomers (e.g., ethylenically unsaturated hydrocarbons such as acrylic monomers and methacrylic monomers) or polymers, some or which are biodegradable or which contain biodegradable units or subunits. Specific medical applications of these radiation-crosslinked, biodrgradable, synthetic hydrogels include applicatins wherein the hydrogel is used for hemostasis, tissue augmentation, tissue engineering, embolization, closure of vascular punctures or wounds and other medical applications.

29 Claims, No Drawings

RADIATION CROSS-LINKED HYDROGELS

FIELD OF THE INVENTION

The present invention relates generally radiation-crosslinked, hydrogel materials and methods for using such materials in biomedical or other applications such as for packaging.

BACKGROUND OF THE INVENTION

Hydrogel polymers have found widespread use in the biomedical materials industry as implant materials in both vascular and tissue environments. They are readily fabricated into a variety of morphologies and can exhibit a range of properties depending on their constituents. Their defining feature is the ability to absorb and hold water, a property which is dominated by the presence of hydrophilic groups in the bulk material.

The prior art has included a number of hydrogels that are radiation crosslinked. These radiation crosslinked hydrogels have typically been prepared by by irradiating aqueous solutions of natural and synthetic polymers to cause crosslinking of the polymer chains. Medically, radiation crosslinked hydrogels are primarily used externally, as medical electrode assemblies and as wound dressings. U.S. Pat. No. 5,354,790 discloses formulations of radiation crosslinked hydrogels in the art. U.S. Pat. No. 5,634,943 discloses a formulation of a radiation crosslinked hydrogel for internal use as a corneal implant.

Many hydrogels of the prior art have been prepared from natural materials. The use of hydrogels derived from natural substances in medical implant applications can be problematic due to inherent variability and/or impurities in the natural product and/or the need for laborious and expensive extraction, isolation and refinement of the desired compound(s) or material(s) from the naturally occurring material. Also, in many biomedical applications, such as those where the hydrogel material is implanted into the body of a human or veterinary patient, it is desirable for the hydrogel biodegrade following implantation. However the crosslinkages formed by radiation crosslinking are typically very stable under physiological conditions and do not biodegrade. Thus, if the advantages of a radiation crosslinked hydrogel and biodegradation are desired, it is necessary to introduce regions susceptible to biodegradation to the precursor polymer and/or monomer.

Accordingly, there remains a need in the art for the development of a synthetic; radiation crosslinked hydrogels that are biodegradable and useable in various applications, including, but not limited to, medical implant applications wherein the hydrogel is used as or in conjunction with vascular puncture sealing, tissue engineering, tissue augmentation (cosmetic body sculpting), surgical sealant, hemostatic agents, drug delivery, and packing materials.

SUMMARY OF THE INVENTION

Hydrogel materials of the present invention are prepared by irradiating an aqueous solution of synthetically prepared polymer(s) or monomer(s), at least some of which (or portions of which) are degradable under physiological conditions (e.g., conditions encountered when the hydrogel material is implanted in the intended location within or on the body of a human or veterinary patient). This resultants in formation of a radiation-crosslinked, biodrgradable, synthetic hydrogel that is useable in a variety of medical and non-medical applications. Examples of synthetically prepared polymers that may be crosslinked to form these hydrogels include poly(ethylene glycol), poly(ethylene oxide), poly(ethylene glycol-co-propylene glycol), poly (vinyl pyrrolidinone), poly(vinyl alcohol), acrylic polymers, and methacrylic polymers. Examples of synthetically prepared monomers that may be crosslinked to form these hydrogels include ethylenically unsaturated hydrocarbons such as acrylic monomers and methacrylic monomers.

In accordance with the present invention, when the radiation-crosslinked, biodrgradable, synthetic hydrogel is prepared from polymeric starting materials, degradable moieties or segments may be incorporated into at least some of the polymeric starting materials prior to irradiation. On the other hand, when the hydrogel is formed from monomeric starting materials; a degradable element or moiety may be introduced or incorporated into the hydrogel concurrently with the irradiation. Further in accordance with the present invention, when the crosslinked hydrogel is to be implanted into the body of a mammal, the formulation or structure of the hydrogel may be selected to ensure that the degradation products that result from biodegradation of the hydrogel will be cleared by the patient's kidneys without causing significant kidney damage. Generally, degradation products that have molecular weights of less than 20,000–30,000 can be cleared by human kidneys without causing significant kidney damage, whereas those having molecular weights in excess of 30,000 typically are not cleared and/or cause significant renal damage.

Still further in accordance with the invention, there is provided a biodegradable, radiation crosslinked PEG hydrogel. This biodegradable, radiation crosslinked PEG hydrogel may be formed by a method comprising the steps of a) reacting monomethoxy-poly(ethylene glycol)(mPEG) with a diacid chloride such as succininc or glutaric chloride to form mPEG dimer, b) dissolving the mPEG dimer in phosphate buffer or other suitable aqueous solvent to provide an aqueous mPEG dimer solution having a pH of approximately 5, c) removing dissolved and/or gaseous oxygen from the mPEG dimer solution by bubbling argon through the solution or by other suitable means and d) irradiating the mPEG dimer solution with ionizing radiation, such as electron beam (EB) radiation of sufficient intensity and for sufficient time to cause a desired amount of crosslinkages to from between molecules of the mPEG dimer.

Still further in accordance with this invention, there are provided methods for treating various diseases, conditions, malformations, or disorders of human or veterinary patients by implanting (e.g. injecting, instilling, implanting surgically or otherwise, introducing through a cannula, catheter, needle or other introduction device or otherwise placing) radiation-crosslinked hydrogels of the foregoing character upon or within the body of the patient. Specifically, the radiation crosslinked hydrogels of the present invention may be implanted subcutaneously, in a wound, in a tumor or blood vessels that supply blood to the tumor, in an organ, in an aberrant blood vessel or vascular structure, in a space located between or among tissues or anatomical structures or within a surgically created pocket or space. In this manner, the radiation crosslinked hydrogels of the present invention are useable for hemostasis, tissue augmentation, embolization, vascular puncture closure, and other medical applications.

Further aspects of this invention will become apparent to those of skill in the art upon reading of the detailed description of exemplary embodiments set forth herebelow.

DETAILED DESCRIPTION OF EXEMPLARY EMBODIMENTS

The following detailed description and examples are provided for the limited purpose of illustrating exemplary embodiments of the invention and not for the purpose of exhaustively describing all possible embodiments of the invention.

Set forth herebelow are examples of methods for preparing synthetic, biodegradable, radiation crosslinked hydrogels of the present invention, as well as some examples of methods for using such hydrogel in certain biomedical applications. The synthetic, biodegradable, radiation-crosslinked hydrogels of the present invention may be prepared from either polymeric or monomeric starting materials, and detailed examples of both types of processes are provided herebelow:

Synthesis of Biodegradable, Radiation-Croslinked Hydrogel from Polymeric Starting Materials 1. Preparation of a Macromeric Solution Initially, a macromeric solution, comprised of aqueous or nearly aqueous solutions of polymers, is prepared. The macromer is comprised of two distinct regions, a water soluble region and a biodegradable region.

The macromer can be any biocompatible, water soluble polymer, including poly(ethylene glycol), poly(ethylene oxide), poly(ethylene glycol-co-propylene glycol), poly(vinyl pyrrolidinone), poly(vinyl alcohol), poly(ethyloxazoline), acrylic polymers, and methacrylic polymers. In a preferred embodiment, the macromer is poly(ethylene glycol). Poly(ethylene glycol) (PEG)is preferred due to its biocompatibility, ready availability in a variety of molecular weights, and its hydroxyl groups for covalently coupling the degradable moiety. Monofunctional macromers, such as monomethoxyPEG (mPEG), are particularly preferred. Preferred macromeric molecular weights range from about 2,000 to about 30,000, more preferably about 2,000 to about 15,000, most preferably about 2,000 to about 5,000.

The degradable moiety is incorporated into the macromer to impart biodegradation. The degradable moiety may undergo degradation by hydrolysis or by enzymatic action. The rate of degradation can be controlled by selecting the type of degradable region or moiety. For example, one method of imparting biodegradation is by joining two molecules of the macromer with linkages that are susceptible to hydrolysis. Examples of hydrolytically-degradable linkages that may be used include ester, peptide, anhydride, orthoester, phosphazine, and phosphoester bonds.

Also, The degradable regions can be comprised of polymer or oligomers of glycolide, lactide, $\epsilon$-caprolactone, other hydroxyacids, and other biologically degradable polymers that yield byproducts that are non-toxic. Preferred poly($\alpha$-hydroxy acids) are poly(glycolic acid), poly(DL-lactic acid), and poly(L-lactic acid). Other potential degradable regions are comprised of poly(amino acids), poly(anhydrides), poly(orthoesters), poly(phosphazines), and poly(phosphoesters). Polylactones such as poly($\epsilon$-caprolactone), poly($\delta$-valerolactone), and poly($\gamma$-butyrolactone) are also useful.

Alternatively, enzymatically degradable regions can be used. Examples of enzymatically degradable regions that can be incorporated include the peptide sequences such as Leu-Gly-Pro-Ala (linkage susceptible to degradation by collagenase) or Gly-Pro-Lys (linkage susceptible to degradation by plasmin) and/or enzymatically degradable peptide sequences as disclosed in West, Pratt and Hubbell, *Protolytically Degradable Hydrogels*, 23$^{rd}$ Annual Meeting of the Society for Biomaterials (1997), the entirety of which is expressly incorporated herein by reference.

Once the macromer has been synthesized, an aqueous, or nearly aqueous, solution of the macromer is prepared. The solution can be prepared in water, saline, buffered saline (e.g. phosphate, carbonate, etc.), or mixtures of the above liquids with small amounts of a pharmaceutically acceptable solvent (e.g. dimethylsulfoxide, ethanol, etc.). Preferred concentrations of the macromer range from approximately 5% w/w to approximately 30% w/w.

Optionally, if the degradable moiety is susceptible to hydrolysis, the pH of the solution can be adjusted to reduce the rate of hydrolysis before implantation into or upon a mammalian body. The macromeric solution is then packaged in an airtight container. The container should be selected with care, as the hydrogel will conform to the shape of the container.

2. Crosslinking of the Macromers

The macromeric solution is then irradiated with ionizing radiaiton. The radiation causes the formation of free radicals at locations along the polymer chains and, at those free radical sites, the chains become crosslinked together. The source of the radiation could be an electron beam generator, gamma ray source, or a van de Graaff generator. Preferred dosages of radiation range from about 10 kGy to about 50 kGy. The exact radiation dosage is dependent upon the molecular weight and concentration of the macromeric solution as well as the desired mechanical properties of the resulting hydrogel. The mechanical properties of the hydrogel are controlled by the crosslink density. The crosslink density can best be manipulated through the macromer molecular weight, macromer concentration, and radiation dose. For most macromers, the crosslink. density can be increased with increasing molecular weight, concentration, and radiation dose. However for PEG based hydrogels, crosslink density is inversely proportional to the concentration of PEG. Optimization of these three variables will be required on an indication by indication basis.

3. Optional Drying or Lypohylization, Trituration and Storage

If desired, the hydrogel may be dried or, lyophilized, ground or broken into particles, and preferably stored in an inert atmosphere to enhance long term stability.

EXAMPLE 1

Preparation of a Biodegradable PEG Hydrogel form mPEG-SA-mPEG Macromer

A 500 mL round bottom flask is charged with 50 g mPEG 5,000 (Union Carbide) and 500 mL toluene (Aldrich).

Approximately 100 mL toluene is azeotropically distilled to remove water from the solution. The solution is cooled to approximately 10° C. Succinic chloride (0.78 g, Aldrich) and triethylamine (1.00 g, Aldrich) are added to the solution. The reaction is then allowed to proceed for 48 hr at room temperature, resulting in precipitate formation.

The precipitate is removed by vacuum filtration with a fritted funnel. The mPEG dimer is then precipitated by adding the solution to 2 L of 4° C. isopropyl alcohol (Aldrich). The precipitated mPEG dimer is collected by vacuum filtration with a fritted funnel. The dissolution in toluene/precipitation in isopropyl alcohol was repeated for three times. Finally, the mPEG dimer is dried in a vacuum oven at 50° C.

The macromer solution is prepared by dissolving 17.5 g of the mPEG dimer in 82.5 g of 50 mM sodium phosphate pH 5. After dissolution is complete, the solution is degassed under vacuum. The macromer solution is then placed into 5 cc syringes (Becton-Dickinson) and capped. The syringes are irradiated with 30 kGy of electron beam radiation (Nutek, Inc., Hayward, Calif.), thereby forming the synthetic, biodegradable, radiation crosslinked hydrogel.

Applications of Hydrogels of the Present Invention

The following are examples of some of the biomedical applications of the biodegradable, radiation crosslinked hydrogel described above. It will be appreciated, however, that this hydrogel material has many other medical and non-medical applications in addition to the specific examples set forth herebelow.

Vascular Puncture Closure

For vascular puncture closure, a hydrogel with high adhesivity and high cohesiveness is desired. The hydrogel must adhere firmly to the subcutaneous tissues to seal the arteriotomy under arterial pressure. Furthermore, the hydrogel must have sufficient cohesive strength to prevent fragmentation under arterial pressure. Degradation of the hydrogel should occur within 1 month post-operative. Another preferred characteristic of the hydrogel for vascular puncture closure is extrudability, namely being able to be injected through no larger than a 6 Fr lumen. A preferred macromer for vascular puncture closure is a dimer of mPEG 10,000 with poly(glycolide) as a degradable linking group. A preferred formulation for vascular puncture closure is approximately 15% w/w solution of the macromer irradiated at approximately 25 kGy and maintained in a flowable, wet state.

Embolization

For embolization of tumors, arterio-venous fistula, sites of trauma or iatrogenic hemorage, etc., a hydrogel of the present invention having high cohesivity and low adhesivity is desired. The hydrogel preferably will remain intact for a period of time (e.g., several years) before it biodegrades and preferably will not deform under arterial pressure. The rate of degradation of the hydrogel may be selected or optimized for each particular embolization indication. In this regard, the rate of degredation of the hydrogel is dependent upon the type and number of biodegradable segments. If rapid biodegredation is desired, lactide or poly(lactide) may be used as a preferred biodegradable segment. If relatively slow biodegredation is desired,ε-caproloctone may be used as a preferred biodegradable segment. A preferred hydrogel for many embolozation applications may comprise dimers of mPEG 5,000 joined together by succinic chloride linking group groups (i.e., degradable moieties). A preferred formulation for embolization is approximately 25% w/w solution of the macromer irradiated at approximately 35 kGy, dried or lyophilized and formed into particles of approximately 100 to 900 microns in diameter.

Surgical or Hemostatic Sponge

As a surgical sponge, a hydrogel with high cohesiveness and some adhesiveness is desired. The hydrogel must remain intact and not deform under arterial pressure. A quick rate of degradation of a surgical sponge is desired. A preferred macromer for sponges is a dimer of mPEG 5,000 with succinic chloride as a degradable linking group. A preferred formulation for embolization is approximately 20% w/w solution of the macromer irradiated at approximately 30 kGy and dried in a sheet of desired thickness, for example approximately 0.5 cm thick. The sheet may be cut into individual sponges of desired sizes and/or shapes.

Surgical Sealant

As a surgical sealant, a hydrogel of the present invention having high adhesivity and high cohesivity is desired. Such surgical sealant may be used to repair leaking lung tissue, close endoleaks of endovascular grafts, seal leakage around sutures, staples, etc. In these applications, the hydrogel must adhere firmly to tissue to seal the fluid leak. Furthermore, the hydrogel must have sufficient cohesive strength to prevent fragmentation under load. Degradation of the hydrogel should occur within 1 month post-operative. A preferred macromer for a surgical sealant is a dimer of mPEG 10,000 with poly(glycolide) as a degradable linking group. A preferred formulation for a surgical sealant is approximately 15% w/w solution of the macromer irradiated at approximately 25 kGy and maintained in a wet, flowable state for application to the desired tissue surface.

Flowable Hemostatic Agent

For use as flowable hemostatic agents, hydrogels of the present invention having high adhesivity and high cohesivity is desired. The hydrogel must adhere firmly to tissue to seal the blood leak. Furthermore, the hydrogel must have sufficient cohesive strength to prevent fragmentation under load. Optionally, thrombin may be incorporated into the hydrogel to aid hemostasis. Degradation of the hydrogel should occur within 1 month post-operative. A preferred macromer for a hemostatic agent is a dimer of mPEG 10,000 with poly(glycolide) as a degradable linking group. A preferred formulation for a hemostatic agent is approximately 15% w/w solution of the macromer irradiated at approximately 25 kGy and maintained in a wet, flowable state.

Temporary Tissue Augmentation

For use in tissue augmentation applications, biodegradable hydrogels of the present invention having high cohesivity and no adhesivity are desired. The hydrogels used in these applications will preferably remain in tact for approximately 1 week to 1 year before biodegrading and preferably will not migrate from the original site of implantation. For tissue augmentation, a slow rate of degradation of is desired. A preferred macromer for tissue augmentation is a dimer of mPEG 5,000 with succinic chloride as a degradable linking group. A preferred formulation for embolization is approximately 20% w/w solution of the macromer irradiated at approximately 35 kGy. Examples of applications where such temporary tissue augmentation may be used include cosmetic lip enlargement, wrinkle reductions and other applications where collagen injections are currently used.

Tissue Engineering

For tissue engineering, a hydrogel with high cohesivity and no adhesivity is desired. The hydrogel must remain intact and not migrate. For tissue engineering, a moderate of degradation of is desired. The effect of the hydrogel matrix may be enhanced by the incorporation of gene therapy. vectors and/or matrix proteins or peptides. A preferred macromer for tissue augmentation is a dimer of mPEG 5,000 with poly(lactide) as a degradable linking group. A preferred formulation for embolization is approximately 20% w/w solution of the macromer irradiated at approximately, 35 kGy.

Drug Delivery

For drug delivery, a hydrogel with high cohesivity and moderate adhesivity is desired. The hydrogel must remain intact and remain where placed. The rate of degradation of the hydrogel would be dependent upon the particular drug being delivered. A preferred macromer for drug delivery is a dimer of mPEG 5,000 with succinic chloride as a degradable linking group. A preferred formulation for embolization is approximately 20% w/w solution of the macromer irradiated at approximately 30 kGy.

The foregoing detailed description is intended to describe certain examples of the invention only and is not intended to be an exhaustive description of all possible embodiments of the invention. It is top be appreciated that various changes, modifications and alterations may be made to the above-set-forth description without departing from the intended spirit and scope of the invention.

What is claimed is:

1. A method for treating a disease, deformation or disorder of a human or veterinary patient, said method comprising the steps of:
   (A) providing a quantity of a biocompatible, hydrophilic polymer which biodegrades to form polymer fragments that are of sufficiently low molecular weight to undergo renal clearance without causing substantial irreversible damage to the patient's kidneys;
   (B) irradiating the polymer so as to cause crosslinking of the polymer; and,
   (C) introducing the crosslinked polymer into or onto the patient's body.

2. A method according to claim 1 wherein Step A comprises providing a synthetic hydrophilic polymer.

3. A method according to claim 1 wherein the crosslinked polymer is biodegradable.

4. A method according to claim 3 wherein the crosslinked polymer biodegrades to form polymer fragments that are of sufficiently low molecular weight to undergo renal clearance without causing substantial irreversible damage to the patient's kidneys.

5. A method according to claim 3 wherein the polymer provided in Step A is dimerized prior to performance of Step B to form a dimer that has biodegradable dimer bonds and wherein Step B comprises irradiating the dimer with radiation effective to cause crosslinking of the dimer molecules.

6. A method according to claim 1 wherein the polymer provided in Step A is a polymerized polyhydric alcohol.

7. A method according to claim 6 wherein the polymer provided in Step A is poly(ethylene glycol).

8. A method according to claim 6 wherein the polymer provided in Step A comprises poly(propylene glycol).

9. A method according to claim 7 further comprising the step of dimerizing the poly(ethylene glycol) provided in Step A to form poly(ethylene glycol) dimer having biodegradable dimer bonds and wherein Step B comprises irradiating the poly(ethylene glycol) dimer.

10. A method according to claim 9 wherein the poly(ethylene glycol) provided in Step A comprises monomethoxy-poly(ethylene glycol) and wherein the monomethoxy-poly(ethylene glycol) is dimerized prior to Step B by:
   i. reacting the monomethoxy-poly(ethylene glycol) with a diacid chloride to form monomethoxy-poly(ethylene glycol) dimer;
   ii preparing an aqueous solution containing the monomethoxy-poly(ethylene glycol) dimer and having a pH of about 5;
   iii. removing any dissolved oxygen from the monomethoxy-poly(ethylene glycol) dimer aqueous solution; and,
   iv. irradiating the monomethoxy poly(ethylene glycol) dimer solution with radiation to crosslink the monomethoxy-poly(ethylene glycol) dimer molecules.

11. A method according to claim 10 wherein Step i is performed by:
   (a) dissolving the monomethoxy-poly(ethylene glycol) in a solvent;
   (b) adding the diacid chloride and a chloride scavenger; allowing the dimerization reaction to proceed; and,
   (c) percipitating out the monomethoxy-poly(ethylene glycol) dimer.

12. A method according to claim 11 wherein the solvent in which the monomethoxty poly(ethylene glycol) is dissolved is toluene.

13. A method according to claim 12 further comprising: distilling off a portion of the toluene prior to addition of the diacid chloride and chloride scavenger.

14. A method according to claim 11 wherein the diacid chloride is succinic chloride.

15. A method according to claim 11 wherein the diacid chloride is glutaric chloride.

16. A method according to claim 13 wherein the chloride scavenger is triethylamine.

17. A method according to claim 8 wherein Step ii is performed by dissolving the monomethoxy-poly(ethylene glycol) in phosphate buffer having a pH of approximately 5.

18. A method according to claim 17 wherein each 17.5 g of monomethoxy-poly(ethylene glycol) is dissolved in approximately 82.5 g of 50 mM phosphate buffer having a pH of approximately 5.

19. A method according to claim 8 wherein Step iii is performed by bubbling argon through the solution for a sufficient time to remove substantially all dissolved oxygen from the solution.

20. A method according to claim 8 wherein Step iv comprises placing the solution in a closed radiation-permiable container and subsequently passing radiation through the container to irradiate the solution.

21. A method according to claim 20 wherein the container is a glass syringe.

22. A method according to claim 8 wherein Step iv comprises irradiating the solution with electron beam radiation.

23. A method according to claim 8 wherein Step iv comprises irradiating the solution with 30 kGy electron beam radiation.

24. A method according to claim 1 wherein the method is carried out for the purpose of wound closure and Step C comprises placing a quantity of the radiation crosslinked hydrogel in a wound.

25. A method according to claim 1 wherein the method is carried out for the purpose of embolizing a blood vessel or other anatomical conduit having a lumen and wherein Step C comprises placing a quantity of the radiation crosslinked hydrogel in the lumen of the blood vessel or anatomical conduit to block flow therethrough.

26. A method according to claim 1 wherein the method is carried out for the purpose of absorbing body fluid and Step C comprises placing a quantity of the radiation crosslinked hydrogel in or on an area of the patient's body from which it is desired to absorb fluid.

27. A method according to claim 1 wherein the method is carried out for the purpose of sealing and Step C comprises placing a quantity of the radiation crosslinked hydrogel in or on the area of the patient's body desired to be sealed.

28. A method according to claim 1 wherein the method is carried out for the purpose of hemostasis and Step C comprises placing a quantity of the radiation crosslinked hydrogel in or on the site of bleeding so as to effect hemostasis at the site of bleeding.

29. A method according to claim 1 wherein the method is carried out for the purpose of tissue augmentation and wherein Step C comprises placing the radiation crosslinked hydrogel in or on the portion of the patient's body where tissue augmentation is desired.

* * * * *